(12) United States Patent
Albertson et al.

(10) Patent No.: US 6,664,057 B2
(45) Date of Patent: Dec. 16, 2003

(54) AMPLICON IN THE 20Q13 REGION OF HUMAN CHROMOSOME 20 AND USES THEREOF

(75) Inventors: Donna G. Albertson, Lafayette, CA (US); Daniel Pinkel, Walnut Creek, CA (US); Colin Conrad Collins, San Rafael, CA (US); Joe W. Gray, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/896,070

(22) Filed: Jun. 28, 2001

(65) Prior Publication Data

US 2002/0120526 A1 Aug. 29, 2002

Related U.S. Application Data

(62) Division of application No. 09/134,044, filed on Aug. 14, 1998, now abandoned.

(51) Int. Cl.[7] .......................... C12Q 1/68; C07H 21/04; C12P 19/34
(52) U.S. Cl. .................. 435/6; 536/23.1; 536/24.32; 536/24.33; 435/91.1; 435/91.2
(58) Field of Search .................. 435/6, 91.1, 91.2; 536/23.1, 24.3, 24.32, 24.33

(56) References Cited

U.S. PATENT DOCUMENTS 5,892,010 A 4/1999 Gray et al.
5,976,790 A * 11/1999 Pinkel et al. ................. 435/6

FOREIGN PATENT DOCUMENTS

WO   WO 98/02539    1/1998
WO   98/02539    *  1/1998

OTHER PUBLICATIONS

Collins et al., "Postional cloning of ZNF217 and NABC1: Genes amplified at 20q13.2 and overexpressed in breast carcinoma", Natl. Acad. of Sci., vol. 95, pp. 8703–8708 (1998).*
Weissenbach, GenBank Acc. No. Z66824.*
Hudson, GenBank Acc. No. G07189.*
Anzick, et al., "AIB1, a steroid receptor coactivator amplified in breast and ovarian cancer," *Science*, 277(5328):965–8 (1997).
Bärland, et al., "Increased Copy No. at 17q22–q24 by CGH in Breast Cancer is Due to High–Level Amplification of Two Separate Regions," *Genes, Chromosomes & Cancer*, 20:372–376 (1997).
Benz, et al., "Expression of c–myc, c–Ha–ras1, and c–erbB–2 proto–oncogenes in normal and malignant human breast epithelial cells," *J Natl Cancer Inst*, 81(22):1704–9 (1989).

Berns, et al., "Oncogene amplification and prognosis in breast cancer: relationship with systemic treatment," *Gene*, 159(1):11–18 (1995).
Bischoff, et al., "A homologue of Drosophila aurora kinase is oncogenic and amplified in human colorectal cancers," *EMBO Journal*, 17:3052–3065 (1998).
Bockmuhl, et al., "[Genetic screening of head–neck carcinomas using comparative genomic hybridization (CGH)]" *Laryngorhinootologie*, 75(7):408–14 (1996).
Borg, et al., "ERBB2 amplification in breast cancer with a high rate of proliferation," *Oncogene*, 6(1):137–43 (1991).
Borg, et al., "c–myc Amplification is an Independent Prognostic Factor in Postmenopausal Breast Cancer," *Int. J. Cancer*, 51:687–691 (1992).
Brinkmann, et al., "The human CAS (cellular apoptosis susceptibility) gene mapping on chromosome 20q13 is amplified in BT474 breast cancer cells and part of aberrant chromosomes in breast and colon cancer cell lines," *Genome Res*, 6(3):187–94 (1996).
Collins, et al., "Positional cloning of ZNF217 and NABC1: Genes amplified at 20q13.2 and overexpressed in breast carcinoma," *Proc. Natl. Acad. Sci USA*, 95:8703–8708 (1998).
Courjal, et al., "DNA amplifications at 20q13 and MDM2 define distinct subsets of evolved breast and ovarian tumours," *Br J Cancer*, 74(12):1984–9 (1996).
Courjal, et al., "Mapping of DNA Amplifications at 15 Chromosomal Localizations in 1875 Breast Tumors: Definition of Phenotypic Groups," *Cancer Research*, 57:4360–4367 (1997).
Dib, et al., "A comprehensive genetic map of the human genome based on 5,264 microsatellites," *Nature*, 380(6570):152–4 (1996).
Dutrillaux, et al., "Characterization of chromosomal anomalies in human breast cancer. A comparison of 30 paradiploid cases with few chromosome changes," *Cancer Genet Cytogenet.*, 49(2):203–17 (1990).
Gaudray, et al., "DNA amplification at 11q13 in human cancer: from complexity to perplexity," *Mutat Res*, 276(3):317–28 (1992).

(List continued on next page.)

Primary Examiner—Gary Benzion
Assistant Examiner—Cynthia Wilder
(74) Attorney, Agent, or Firm—Townsend and Townsend and Crew LLP

(57) ABSTRACT

This invention pertains to the field of cancer genetics and cytogenetics. In particular, this invention pertains to the identification of a novel amplicon on human chromosome 20 which is associated with cancer. More particularly this invention pertains to the identification of a novel "amplicon" or genomic nucleic acid in a region of amplification at about 20q13.2 which has been associated with a variety of cancers, particularly breast cancer. The novel amplicon of the invention can be used as a probe specific for this region of 20q13.2 as well as for the diagnosis and prognosis of various cancers. Also provided are kits for screening for the presence and copy number of the novel amplicon of the invention in a sample containing human nucleic acid.

16 Claims, 2 Drawing Sheets

OTHER PUBLICATIONS

Guan, et al., "Hybrid Selection of Transcribed Sequences from Microdissected DNA: Isolation of Genes within an Amplified Region at 20q11–q13.2 in Breas Cancer," *Cancer Research*, 56:3446–3450 (1996).

Isola, et al., "Genetic aberrations detected by comparative genomic hybridization predict outcome in node–negative breast cancer," *Am J Pathol*, 147(4):905–11 (1995).

Iwabuchi, et al., "Genetic analysis of benign, low–grade, and high–grade ovarian tumors," *Cancer Res*, 55(24):6172–80 (1995).

Kallioniemi, et al., "Detection and mapping of amplified DNA sequences in breast cancer by comparative genomic hybridization," *Proc Natl Acad Sci USA*, 91(6):2156–60 (1994).

Letovsky, et al., "GDB: the Human Genome Database," *Nucleic Acids Res*, 26(1):94–9 (1998).

Muleris, et al., "Detection of DNA amplification in 17 primary breast carcinomas with homogeneously staining regions by a modified comparative genomic hybridization technique," *Genes Chromosomes Cancer*, 10(3):160–70 (1994).

Olson, et al., "A common language for physical mapping of the human genome," *Science*, 245(4925):1434–5 (1989).

Reid, et al., "A 1–Mb Physical Map and PAC Contig of the Imprinted Domain in 11p15.5 That Contains TAPA1 and the BWSCR1/WT2 Region," *Genomics*, 43:366–375 (1997).

Reznikoff, et al., "Long–term genome stability and minimal genotypic and phenotypic alterations in HPV16 E7–, but not E6–, immortalized human uroepithelial cells," *Genes Dev*, 8(18):2227–40 (1994).

Savelieva, et al., "20q gain associates with immortalization: 20q13.2 amplification correlates with genome instability in human papillomavirus 16 E7 transformed human uroepithelial cells," *Oncogene*, 14(5):551–60 (1997).

Schlegel, et al., "Comparative genomic in situ hybridization of colon carcinomas with replication error," *Cancer Res*, 55(24):6002–5 (1995).

Sen, et al., "A putative serine/threonine kinase encoding gene BTAK on chromosome 20q13 is amplified and overexpressed in human breast cancer cell lines," *Oncogene*, 14(18):2195–200 (1997).

Smith HS, et al., "Molecular and cellular lesions associated with breast cancer progression," *Breast Cancer Res. Treat.*, 18 Suppl 1:S51–4 (1991).

Solinas–Toldo, et al., "Matrix–based comparative genomic hybridization: biochips to screen for genomic imbalances," *Genes Chromosomes Cancer*, 20(4):399–407 (1997).

Solinas–Toldo, et al., "Specific chromosomal imbalances in human papillomavirus–transfected cells during progression toward immortality," *Proc Natl Acad Sci USA*, 94(8):3854–9 (1997).

Stokke, et al., "A physical map of chromosome 20 established using fluorescence in situ hybridization and digital image analysis," *Genomics*, 26(1):134–7 (1995).

Tanner, et al., "Amplification of chromosomal region 20q13 in invasive breast cancer: prognostic implications," *Clin Cancer Res*, 1(12):1455–61 (1995).

Tanner, et al., "Increased copy number at 20q13 in breast cancer: defining the critical region and exclusion of candidate genes," *Cancer Res*, 54(16):4257–60 (1994).

Tanner, et al., "Independent amplification and frequent co–amplification of three nonsyntenic regions on the long arm of chromosome 20 in human breast cancer," *Cancer Res*, 56(15):3441–5 (1996).

Tirkkonen, et al., "Molecular Cytogenetics of Primary Breast Cancer by CGH," *Genes, Chromosomes & Cancer*, 21:177–184 (1998).

Van de Vijver and Nusse, "The molecular biology of breast cancer," *Biochim Biophys Acta*, 1072(1):33–50 (1991).

Weissenbach, et al., "A second–generation linkage map of the human genome," *Nature*, 359(6398):794–801 (1992).

Williamson, et al., "Chromosomal mapping of the human and mouse homologues of two new members of the AP–2 family of transcription factors," *Genomics*, 35(1):262–4 (1996).

* cited by examiner

AMPLICON IN THE 20Q13 REGION OF HUMAN CHROMOSOME 20 AND USES THEREOF

The present application is related to U.S. patent application Ser. No. ("USSN") 08/680,395, filed Jul. 15, 1996; and U.S. Ser. No. 08/731,499, filed Oct. 16, 1996. The present application also incorporates by reference each of the aforementioned applications in their entirety and for all purposes.

This invention was made with United States Government support under Grant No. NIH/NCI 5P50CA-58207-06, awarded by the National Institutes of Health. The United States Government has certain rights in this invention.

FIELD OF THE INVENTION

This invention pertains to the field of cancer genetics and cytogenetics. In particular, this invention pertains to the identification of nucleic acid sequences associated with a novel amplicon on human chromosome 20 which is associated with cancer. More particularly this invention pertains to the identification of a novel "amplicon" in a region of genomic nucleic acid amplification at about 20q13. These nucleic acid sequences can be used as probes in the diagnosis and prognosis of various cancers.

BACKGROUND OF THE INVENTION

Chromosome abnormalities are often associated with genetic disorders, degenerative diseases, and cancer. The deletion or multiplication of copies of whole chromosomes and the deletion or amplifications of chromosomal segments or specific regions are common occurrences in cancer (Smith (1991) Breast Cancer Res. Treat. 18: Suppl. 1:5–14; van de Vijer (1991) Biochim. Biophys. Acta. 1072:33–50). In fact, amplifications and deletions of DNA sequences can be the cause of a cancer. For example, proto-oncogenes and tumor-suppressor genes, respectively, are frequently characteristic of tumorigenesis (Dutrillaux (1990) Cancer Genet. Cytogenet. 49: 203–217). Clearly, the identification and cloning of specific genomic regions associated with cancer is crucial both to the study of tumorigenesis and in developing better means of diagnosis and prognosis.

Studies using comparative genomic hybridization (CGH) have revealed approximately twenty amplified genomic regions in human breast tumors (Muleris (1994) Genes Chromosomes Cancer 10:160–170; Kalliioniemi (1994) Proc. Natl. Acad. Sci. USA 91:2156–2160; Isola (1995) Am. J. Pathol. 147:905–911). These regions are predicted to encode dominantly acting genes that may play a role in tumor progression or response to therapy. Three of these amplified regions have been associated with established oncogenes: ERBB2 at 17q12, MYC at 8q24 and CCND1 and EMS1 at 11q13. In breast cancer, ERBB2 and CCND1/EMS1 amplification and overexpression are associated with decreased life expectancy (Gaudray (1992) Mutat. Res. 276:317–328; Borg (1991) Oncogene 6:137–143). MYC amplification has been associated with lymph node involvement, advanced stage cancer and an increased rate of relapse (Borg (1992) Intern. J. Cancer 51:687–691; Berns (1995) gene 159:11–18). Clearly, the identification of additional amplified genomic regions associated with breast cancer or other tumor cells is critical to the study of tumorigenesis and in the development of cancer diagnostics.

One of the amplified regions found in the CGH studies was on chromosome 20, specifically, 20q13. Amplification of 20q13 was subsequently found to occur in a variety of tumor types and to be associated with aggressive tumor behavior. Increased 20q13 copy number was found in 40% of breast cancer cell lines and 18% of primary breast tumors (Kalliioniemi (1994) supra). Copy number gains at 20q13 have also been reported in greater than 25% of cancers of the ovary (Iwabuchi (1995) Cancer Res. 55:6172–6180), colon (Schlegel (1995) Cancer Res. 55:6002–6005), head-and-neck (Bockmuhl (1996) Laryngor. 75:408–414), brain (Mohapatra (1995) Genes Chromosomes Cancer 13:86–93), and pancreas (Solinas-Toldo (1996) Genes Chromosomes Cancer 20:399–407). The 20q13 region was analyzed at higher resolution in breast tumors and cell lines using fluorescent in situ hybridization (FISH). A 1.5 megabase (Mb) wide amplified region within 20q13 was identified (Stokke (1995) Genomics 26:134–137); Tanner (1994) Cancer Res. 54:4257–4260). Interphase FISH revealed low-level (>1.5×) and high level (>3×) 20q13 sequence amplification in 29% and 7% of breast cancers, respectively (Tanner (1995) Clin. Cancer Res. 1:1455–1461). High level amplification was associated with an aggressive tumor phenotype (Tanner (1995) supra; Courjal (1996) Br. J. Cancer 74:1984). Another study, using FISH to analyze 14 loci along chromosome 20q in 146 uncultured breast carcinomas, identified three independently amplified regions, including RMC20C001 region at 20q13.2 (highly amplified in 9.6% of the cases), PTPN1 region 3 Mb proximal (6.2%), and AIB3 region at 20q11 (6.2%) (Tanner (1996) Cancer Res. 56:3441–3445). Clearly, definitive characterization of amplified regions within 20q13 would be an important step in the diagnosis and prognosis of these cancers.

Increased copy number of chromosome 20q in cultured cells also has been associated with phenotypes characteristic of progressing tumors, including immortalization and genomic instability. For example, increased copy number at 20q11-qter has been observed frequently in human uroepithelial cells (HUC) (Reznikoff (1994) Genes Dev. 8:2227–2240) and keratinocytes (Solinas-Toldo (1997) Proc. Natl. Acad. Sci. USA 94:3854–3859) after transfection with human papilloma virus (HPV)16 E7 or HPV16, respectively. In addition, increased copy number at 20q13.2 has been associated with p53 independent genomic instability in some HPV16 E7 transfected HUC lines (Savelieva (1997) Oncogene 14:551–560). These studies suggest that increased expression of one or more genes on 20q and especially at 20q13.2 contribute to the evolution of breast cancer and other solid tumors. Several candidate oncogenes have been identified as amplified on 20q, including AIB1 (Anzick (1997) Science 277:965–968), BTAK (Sen (1997) Oncogene 14:2195–200), CAS (Brinkmann (1996) Genome Res. 6:187–194) and TFAP2C (Williamson (1996) Genomics 35:262–264). Clearly, definitive characterization of nucleic acid sequences in 20q13 associated with tumor phenotypes would be an important step in the diagnosis and prognosis of these cancers. The present invention fulfills these and other needs.

SUMMARY OF THE INVENTION

The present invention relates to the identification and genomic mapping of new regions of nucleic acid associated with cancer and tumorigenesis.

The invention provides a novel method for screening for the presence of an amplicon in a sample of human nucleic acid. The first step of this method provides a sample of nucleic acid derived from a human cell and a probe, where the probe comprises nucleic acid which hybridizes specifically to a nucleic acid sequence including from D20S211 through D20S120. The second step involves contacting the human nucleic acid with the probe, where the probe is contacted with the human genomic nucleic acid under conditions in which the probe binds selectively under stringent conditions to the human genomic nucleic acid to form a hybridization complex. The last step is detecting the formation of the hybridization complex. In one embodiment, the human nucleic acid can be genomic DNA, which can be isolated from a breast tumor cell. The detection step can further comprise determining the copy number of the amplicon.

In this method, the probe can also comprise a nucleic acid which hybridizes specifically to a nucleic acid sequence spanning the distance between D20S 120 and D20S211. In alternative embodiments, the probe can comprise a nucleic acid which hybridizes specifically to a STS marker selected from the group consisting of AFMa233wg1, AFM080ya1, AFM069ya1, WI-16748, WI-9939, AFMa072zb9, WI-6578, AFM224zd12, WI-9227, and AFM276xh1. The probe can also comprise a nucleic acid which hybridizes specifically to a GDB locus nucleic acid sequence selected from the group consisting of D20S211, D20S854, D20S876, D20S1044, D20S913, D20S720, and D20S 120. Alternatively, the probe can comprise a nucleic acid which hybridizes specifically to a cloned genomic nucleic acid sequence selected from the group consisting of RMC20B4097, RMC20B4103, RMC20P4016, RMC20B4130, RMC20P4185, RMC20B4188, RMC20B4109, RMC20P4010, RMC20P4028, RMC20P4003, RMC20B4099, RMC20P4018, RMC20P4069, RMC20B4121, RMC20B4087, and RMC20P4070.

In another embodiment, the probe can comprise a polymerase chain reaction primer pair capable of amplifying some or all of the nucleic acid sequence including from D20S211 through D20S120. The detection step can comprise detecting the formation of the polymerase chain reaction amplification reaction. The polymerase chain reaction primer pair can be an STS PCR primer pair selected from the group consisting of AFMa233wg1, AFM080ya1, AFM069ya1, WI-16748, WI-9939, AFMa072zb9, WI-6578, AFM224zd12, WI-9227, and AFM276xh1.

In the methods of the invention the probe can be attached to a solid surface and the attached probe can be a member of a nucleic acid array. The human nucleic acid can be labeled with a detectable composition. The detectable composition can be fluorescein or Texas red. In an alternative embodiment, the probe is labeled with a detectable composition. The method can further provide nucleic acids from a reference cell, wherein the reference cell nucleic acid is contacted with the probe before or simultaneously with the human genomic nucleic acid. The method can further provide Cot-1 DNA, wherein the Cot-1 DNA is hybridized to the human genomic nucleic acid before contacting the human genomic nucleic acid with the probe.

The invention also provides a nucleic acid probe for screening for the presence of an amplicon in a sample of human genomic nucleic acid, comprising a nucleic acid which hybridizes specifically to a nucleic acid sequence including from D20S211 through D20S120. Alternatively the probe can comprise nucleic acid which hybridizes specifically to: the nucleic acid sequence spanning the distance between D20S120 and D20S211; or, a STS marker selected from the group consisting of AFMa233wg1, AFM080ya1, AFM069ya1, WI-16748, WI-9939, AFMa072zb9, WI-6578, AFM224zd12, WI-9227, and AFM276xh1; or, a GDB locus nucleic acid sequence selected from the group consisting of D20S211, D20S854, D20S876, D20S1044, D20S913, D20S720, and D20S120; or, a cloned genomic nucleic acid sequence selected from the group consisting of RMC20B4097, RMC20B4103, RMC20P4016, RMC20B4130, RMC20P4185, RMC20B4188, RMC20B4109, RMC20P4010, RMC20P4028, RMC20P4003, RMC20B4099, RMC20P4018, RMC20P4069, RMC20B4121, RMC20B4087, and RMC20P4070.

In another embodiment, the probe can comprise a polymerase chain reaction primer pair capable of amplifying some or all of the nucleic acid sequence including from D20S211 through D20S120. The polymerase chain reaction primer pair can be an STS PCR primer pair selected from the group consisting of AFMa233wg1, AFM080ya1, AFM069ya1, WI-16748, WI-9939, AFMa072zb9, WI-6578, AFM224zd12, WI-9227, and AFM276xh11.

The invention also provides a kit for screening for the presence of an amplicon in a sample of human nucleic acid, the kit comprising a compartment which contains a probe, wherein the probe comprises nucleic acid which hybridizes specifically to a nucleic acid sequence including from D20S211 through D20S120. Alternatively, the probe can comprise nucleic acid which hybridizes specifically to: sequences which span the distance between D20S120 and D20S211; or, a STS marker selected from the group consisting of AFMa233wg1, AFM080ya1, AFM069ya1, WI-16748, WI-9939, AFMa072zb9, WI-6578, AFM224zd12, WI-9227, and AFM276xh1; or, a GDB locus nucleic acid sequence selected from the group consisting of D20S211, D20S854, D20S876, D20S1044, D20S913, D20S720, and D20S120; or, a cloned genomic nucleic acid sequence selected from the group consisting of RMC20B4097, RMC20B4103, RMC20P4016, RMC20B4130, RMC20P4185, RMC20B4188, RMC20B4109, RMC20P4010, RMC20P4028, RMC20P4003, RMC20B4099, RMC20P4018, RMC20P4069, RMC20B4121, RMC20B4087, and RMC20P4070.

In another embodiment, the probe of the kit can comprise a polymerase chain reaction primer pair capable of amplifying some or all of the nucleic acid sequence including from D20S211 through D20S120. The polymerase chain reaction primer pair can be an STS PCR primer pair selected from the group consisting of AFMa233wg1, AFM080ya1, AFM069ya1, WI-16748, WI-9939, AFMa072zb9, WI-6578, AFM224zd12, WI-9227, and AFM276xh1. The probe can be a cloned human nucleic acid, and the cloned human genomic nucleic acid can be attached to a solid surface. The attached probe can be a member of a nucleic acid array. The kit can further comprises instructional material that indicates that the detection of greater than two amplicon copies in a cell can be diagnostic or prognostic of cancer or tumorigenesis.

A further understanding of the nature and advantages of the present invention may be realized by reference to the remaining portions of the specification, the figures and claims.

All publications, GenBank Accession references (sequences), patents and patent applications cited herein are hereby expressly incorporated by reference for all purposes.

comprise nucleic acid which hybridizes specifically to a nucleic acid sequence, particularly in the 20q13.2 region, including, e.g., from D20S211 through D20S120. In alternative embodiments, the probe can comprise nucleic acid which hybridizes specifically to any nucleic acid sequence spanning the distance between D20S120 and D20S211; to any clone, GDB locus or STS marker in the 20q13.2 region, such as the exemplary clones, GDB loci, STSs, and other markers (e.g., WI-9227) listed in Table 1.

Figure 2:
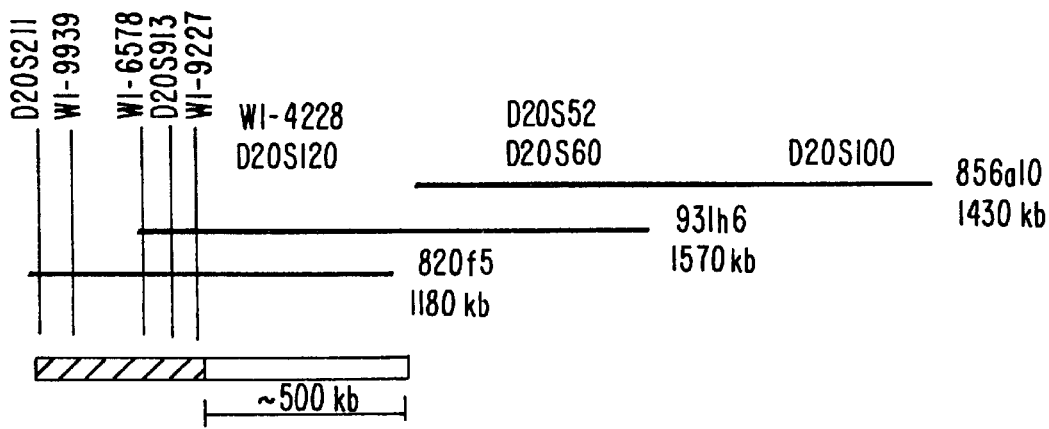
FIG. 2 shows the distribution and location of selected markers and clones in the 20q13.2 region of chromosome 20. Three contiguous YACs containing 20q13 genomic nucleic acid inserts (856a10, 931h6, 820f5) are drawn as horizontal lines.

The terms "D20S120," "D20S211," "D20S193," and similar "D numbers" as used herein (as used, e.g., in Table 1 and FIG. 2), are Genome Database ("GDB") designations that refer to specific genomic nucleic acid sequences mapped to a specific chromosome, see, e.g., Letovsky (1998) *Nucleic Acids Res.* 26:94–99. Information on these loci and STS designations, are available on public databases, see, e.g., http://www.gdb.org/. Table 1 lists the GDB loci and

| High Resolution Clone | Array Clones GDB Locus Name | STS | GDB Locus Name | STS | STS | STS | other |
|---|---|---|---|---|---|---|---|
| RMC20B4166 | D20S902 | AFMc028zc5 | | | | | |
| RMC20P4067 | D20S480 | | D20S1020 | WI-10832 | | | |
| RMC20B4123 | D20S480 | | D20S1020 | WI-10832 | | | |
| RMC20P4041 | D20S480 | | | | | | |
| RMC20P4039 | | | | | | | RMC20C001 |
| RMC20P4030 | D20S183 | AFM248wb9 | D20S854 | AFMa233wg1 | | | |
| RMC20P4009 | | SGC31010 | | WI-16697 | | | |
| RMC20P4007 | | SGC31010 | | WI-16697 | | | |
| RMC20B4097 | D20S854 | AFMa233wg1 | D20S211 | AFM080ya1 | SGC31010 | WI-16697 | |
| RMC20B4103 | D20S211 | AFM080ya1 | | | | | |
| RMC20P4016 | D20S211 | AFM080ya1 | | | | | |
| RMC20B4130 | D20S211 | AFM080ya1 | | | | | |
| RMC20P4185 | | | | | | | |
| RMC20B4188 | D20S876 | AFMb069wg1 | | | | | |
| RMC20B4109 | | | | | | | |
| RMC20P4010 | | WI-16748 | | | | | |
| RMC20P4028 | D20S1044 | WI-9939 | | | | | |
| RMC20P4003 | D20S913 | AFMa072zb9 | D20S720 | WI-6578 | WI-16748 | | |
| RMC20B4099 | D20S913 | AFMa072zb9 | D20S720 | WI-6578 | WI-16748 | | |
| RMC20P4018 | | | | | | | |
| RMC20P4069 | | | | | | | |
| RMC20B4121 | | AFM224zd12 | | | | | |
| RMC20B4087 | | AFM224zd12 | | WI-9227 | | | |
| RMC20P070 | D20S120 | AFM276xh1 | | | | | |

DEFINITIONS

To facilitate understanding the invention, a number of terms are defined below.

The term "amplicon" as used herein refers to a region of genomic nucleic acid which, when present in altered copy number, is associated with cancer. For example, the invention provides novel nucleic acid sequences on human chromosome 20q13.2 which, when present in aberrant copy number, are associated with cancer. Typically, the nucleic acid sequences of the invention have an increased number of copies when associated with cancer, such as breast cancer. Hence, the term "amplicon" for these novel sequences. However, the copy number can also be decreased in some circumstances. Thus, the invention provides a nucleic acid which can be used as a probe to analyze changes in copy number to screen and diagnose cancer. Using high resolution array comparative genomic hybridization ("array CGH"), sequences from the amplicon of the invention can be used as a probe to determine single copy number changes in nucleic acid samples. Determination (quantification) of copy number can also aid in the prognosis of a cancer, as increased amplicon copy number is associated with an aggressive tumor phenotype. In particular, the probes of the invention their corresponding STS names for the clones which comprise the high density array used to identify the novel amplicon of the invention. These GDB loci map to the 20q13.2 region of human chromosome 20. The loci "D20S120," "D20S211," and "D20S 193," are described in further detail below.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology— Hybridization with Nucleic Acid Probes* part I, chapt 2, "Overview of principles of hybridization and the strategy of nucleic acid probe assays," Elsevier, N.Y. ("Tijssen").

Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and detailed discussion, below), with the hybridization being carried out overnight. An example of highly stringent wash conditions is 0.15 M NaCl at 72° C. for about 15 minutes. An example of stringent wash conditions is a 0.2× SSC wash at 65° C. for 15 minutes (see, e.g., Sambrook (1989) *Molecular Cloning: A Laboratory Manual* (2nd ed.) Vol. 1–3, Cold Spring Harbor Laboratory, Cold Spring Harbor Press, NY ("Sambrook") for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example of a low stringency wash for a duplex of, e.g., more than 100 nucleotides, is 4× to 6× SSC at 40° C. for 15 minutes.

The term "labeled with a detectable composition" as used herein refers to a nucleic acid attached to a detectable composition, i.e., a label. The detection can be by, e.g., spectroscopic, photochemical, biochemical, immunochemical, physical or chemical means. For example, useful labels include $^{32}P$, 35S, $^3H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid, peptide or other target compound to be detected, or it can be attached to a probe or antibody which hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) *Mol Cell Probes* 9:145–156.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompasses by the term include methylphosphonate linkages or alternating methylphosphonate and phosphodiester linkages (Strauss-Soukup (1997) *Biochemistry* 36:8692–8698), and benzylphosphonate linkages (Samstag (1996) *Antisense Nucleic Acid Drug Dev* 6:153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on a solid surface to which sample nucleic acids are hybridized. The nucleic acids of a target element can contain sequence from specific genes or clones, such as the probes of the invention, as disclosed herein. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 µm to about 3 mm, preferably between about 5 µm and about 1 mm. The target elements of the arrays may be arranged on the solid surface at different densities. The target element densities will depend upon a number of factors, such as the nature of the label, the solid support, and the like. One of skill will recognize that each target element may comprise a mixture of probe nucleic acids of different lengths and sequences. Thus, for example, a target element may contain more than one copy of a cloned piece of DNA, and each copy may be broken into fragments of different lengths. The length and complexity of the probe nucleic acid fixed onto the target element is not critical to the invention. One of skill can adjust these factors to provide optimum hybridization and signal production for a given hybridization procedure, and to provide the required resolution among different genes or genomic locations. In various embodiments, probe sequences will have a complexity between about 1 kb and about 1 Mb, between about 10 kb to about 500 kb, between about 200 to about 500 kb, and from about 50 kb to about 150 kb.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767–773 (1991); Johnston (1998) Curr. Biol. 8:R171–R174; Schummer (1997) Biotechniques 23:1087–1092; Kern (1997) Biotechniques 23:120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The term "sample of human nucleic acid" as used herein refers to a sample comprising human DNA or RNA in a form suitable for hybridization to probes of the invention. The nucleic acid may be isolated, cloned or amplified; it may be, e.g., genomic DNA, mRNA, or cDNA from a particular chromosome, or selected sequences (e.g. particular promoters, genes, amplification or restriction fragments, cDNA, etc.) within particular amplicons or deletions disclosed here. The nucleic acid sample may be extracted from particular cells or tissues. The cell or tissue sample from which the nucleic acid sample is prepared is typically taken from a patient suspected of having cancer associated with the amplicon amplification or deletion or translocation being detected. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The sample may be isolated nucleic acids immobilized on a solid. The sample may also be prepared such that individual nucleic acids remain substantially intact and comprises.

The term "sequence tagged site" or "STS" refers to a sequence-based method of "tagging," or identifying, cloned DNA segments, such as, e.g., members of contigs, segments that contain unusual restriction sites (members of restriction maps), probes that detect genetically mapped DNA polymorphisms, or sequences that hybridize in situ to particular cytogenetic bands. To assign an STS designation, each cloned DNA segment is sequenced over (at least) an approximately 200 to 500 base pair region. With this sequence data, PCR primers are designed and tested to ensure they can be used to identify, or "tag," that particular sequence by PCR amplification. Submission of segment and primer sequences, and PCR assay conditions to public databases allows anyone to rapidly and conveniently identify—and map—virtually any genomic clone or fragment. See, e.g., Olson (1989) "A common language for physical mapping of the human genome," Science 245:1434–1435.

DETAILED DESCRIPTION OF THE INVENTION

The invention identifies a novel, circumscribed region of nucleic acid within the 20q13.2 region of human chromosome 20 useful for detecting, diagnosing and prognosing human cancers. The nucleic acid regions disclosed herein are often associated with chromosomal abnormalities and copy number changes in human cancers, particularly human breast cancer. These novel regions are termed "amplicons" because they are typically have increased copy numbers in cancer cells. Thus, these novel sequences are used in probes and methods to detect copy number changes to screen for the presence of disease, such as cancer, especially breast cancer. Furthermore, determination of copy number can be used in the prognosis of certain cancers, as high copy number is frequently associated with aggressive tumor behavior and poor response to therapy.

The amplification of a nucleic acid region, or amplicon, is typically driven by a critical minimal "core" gene sequence responsible for the amplified phenotype. In many instances, this critical core gene sequence encodes an oncogene. Thus, identification of the minimal gene sequence driving amplification will likely identify an oncogene. Furthermore, tumors with greatly amplified regions are typically more aggressive tumors, as has been observed with tumors having very amplified 20q13.2 regions. Thus, definition and use of a minimal, or "amplification driving,' amplicon sequence produces new and improved diagnostic and prognostic procedures. Use of smaller, or "minimal" amplicon gene sequence to determine the copy number of that region in a cancer cell results in more accurate results, i.e., better diagnosis and prognosis, than results acquired using larger gene segments. The invention provides such a smaller, minimal "core" region, a novel amplicon, in the 20q13.2 region of chromosome 20—which is distinct from previously described core regions.

High resolution array-based comparative genomic hybridization (array CGH) was applied to analyze copy number variation in the 20q13.2 region of chromosome 20, particularly in cancer cells, such as breast cancer cells. The high resolution mapping of 20q13.2 sequences was accomplished using an array of positionally overlapping clones, termed a "contig." Most of the chromosome 20 inserts of the clones comprising the contig were less than one megabase (Mb) in size, ranging from about 100 to 200 kilobases (Kb). This enabled the array to physically map and quantify circumscribed regions ("amplicons") from a nucleic acid sample to a very high degree of resolution, resulting in the discovery of the novel 20q13.2 amplicon of the invention.

Figure 3:
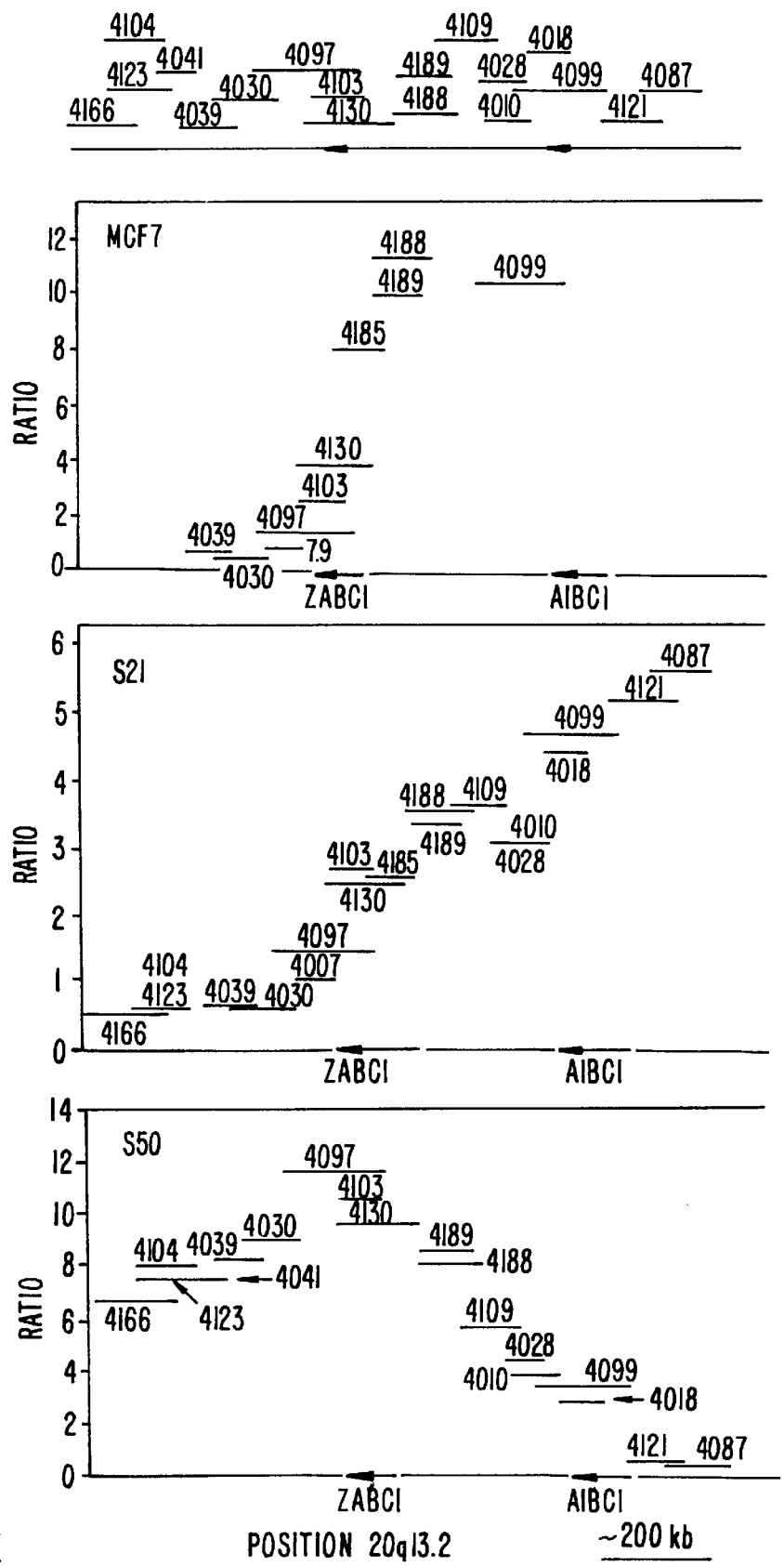
FIG. 3 shows the results of a high resolution array analysis of 20q13.2 using the breast cancer cell line MCF7 (upper panel), and two breast cancer tumors, S21 and S50 (lower two panels). The top panel shows the position of the array probes in the contig. The probe clones in the top panel are listed in Table 1; the clone names have been shortened to the last four digits.

The clones used in the high resolution array that identified the novel amplicon of the invention are shown in the top panel of FIG. 3. This array comprised an overlapping set of clones covering 1.5 Mb. The top panel in FIG. 3 shows the names and relative positions of the clones comprising the contig of this high resolution array (in FIG. 3, probe clone names are abbreviated to the last four digits, i.e., clone RMC20B4097 is abbreviated as "4097"). FIG. 3 illustrates how high resolution array ("CGH") data can assist in localizing smaller, "critical" gene segments within an amplified region, e.g., as the illustrated set of overlapping clones was used in the array to discover the novel 20q13.2 amplicon of the invention. FIG. 3 shows the results of high resolution analysis of breast cancer cell line MCF7 (see, e.g., Benz (1989) *J. Natl. Cancer Inst.* 81:1704–1709) (upper panel), and two tumors, S21 and S50 (lower two panels) (provided by Bay Area Breast Cancer SPORE, UCSF Cancer Center, Univ. of California).

Table 1 further illustrates the various clones of this array ("RMC" clone names, left-hand column) and corresponding GDB locus names ("D numbers"), STS marker designations, and other associated names from the public domain. Some clones contain several STS markers from the public databases (e.g. RMC20P4030). Many STS markers (and their associated PCR primers, see STS definition, above) can be used to identify a GDB locus, designated by a "D number." A "D" locus, e.g., D20S902, can also be associated with another clonal designation, such as AFMc028zc5. Another example is clone RMC20P4009, which contains SGC31010 and WI-16697.

In FIG. 3, the length of the clonally-associated lines on the horizontal axis are proportional to distance along the chromosome. The telomere is to the right. The high resolution array CGH data for MCF7 (top panel), tumor S21 (middle panel) and breast tumor S50 (bottom panel) are plotted with horizontal black bars representing the length of individual clones (probes) and their mapped positions along the chromosome. They are plotted at a vertical height indicating their CGH ratio, i.e., the higher lines have greater copy numbers. The standard deviation of the measurements is estimated to be about 10%.

In cell line MCF7, there is an abrupt copy number increase. Elevated ratios are recorded on the distal portion of clone RMC20B4097 ("4097"), and an increase is detected with clones RMC20B4103 ("4103") and RMC20B4130 ("4130"), which map more distally (see Table 1, e.g., clone 4097 can also be identified by the STS designated AFMa233wg1, and by the GDB marker names D20S211 or D20S854). The copy number becomes constant distally from this amplified region, within the uncertainty in the measurements. These data indicate that in MCF7, there exists a region of high copy number mapping in the most distal part of RMC20B4097 (to the right of "4097"), also partly contained in RMC20B4103 ("4103") and RMC20B4130 ("4130"), and wholly contained in the more distal clones. Thus, the position of an abrupt copy number increase (vertical gray line) can be mapped very precisely from the ratios on the overlapping clones (RMC20B4097, RMC20B4103, and RMC20B4130).

In contrast, tumors S21 and S50 show relatively continuous change in copy number over distances of several hundred kilobases (kb). In tumor S50, a peak in copy number occurs around clone RMC20B4097 ("4097"). The distal boundary (to the right in FIG. 3, towards the telomere) of S50's amplified region maps to about clone RMC20P4028 ("4028") to clone RMC20P4018 ("4018"). For tumor S21, the proximal boundary (to the left) of the amplified region is located at about clone 4097, within the region of contiguous clone coverage in the high resolution array. In S21, copy number continues to increase as one moves more distally (to the right) along the chromosome.

The increasing magnitude in copy number in S21 (and another tumor, S59, these data are not shown in FIG. 3) is striking. It focuses attention on chromosomal regions distal to the contig (to the right in FIG. 3), still proximal to the next marker on the scanning array, D20S120 (D20S120 maps distal to marker RMC20B4087; D20S 120 is contained in RMC20P070; see Table 1). The clone containing GDB marker D20S120 is not elevated in copy number or its copy number is greatly reduced in these tumors (data not shown). For three other tumors, the distal boundary was mapped between D20S120 and the next most distal target clone, D20S100 (data not shown); these also had greatly reduced copy number at D20S120, compared to the other 20q13.2 contig clones. Thus, these observations indicate that the distal boundary of this novel 20q13.2 amplicon generally occurs near D20S120. Moreover, they establish that the distal boundary of the minimal amplified region maps proximal to this locus. Thus, a new amplicon has been identified between (proximal to distal) RMC20B4097 ("4097," or, D20S211, see Table 1) and D20S120 (RMC20P070).

Figure 1:
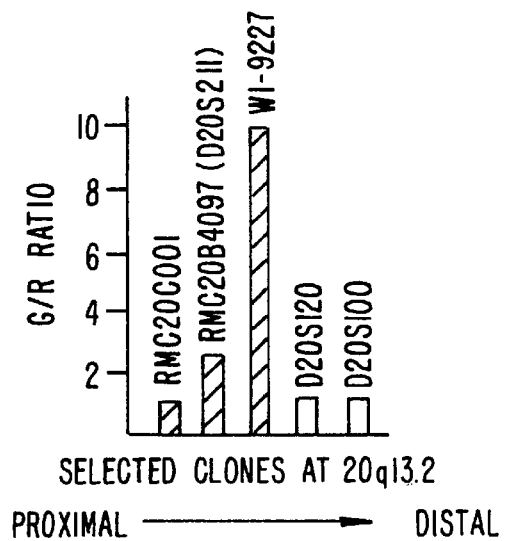
FIG. 1 shows the results of an analysis of the 20q13.2 region of a tumor ("S21") using hybridization analysis. The graphs shows comparative genomic hybridization (CGH) ratios for selected 20q13.2 clones in the tumor S21, indicating the "G/R" or green (fluorescein dCTP) to red (Texas red dCTP) fluorescence ratio as a function of the amount of genomic nucleic acid hybridization to the 20q13.2 contig clones.

The novel amplicon was further characterized using FISH, as shown in FIG. 1. Clones RMC20C001, RMC20B4097 ("4097"), WI-9227, D20S120 and D20S100 were used as probes. Based increased G/R ratios, a circumscribed area of copy number amplification—an amplicon—was detected. The distal boundary of the novel 20q13.2 amplicon was determined to be proximal to D20S120. In arriving at this conclusion, the copy number analysis of tumor sample S21 was the most informative. As shown in FIG. 1, in S21, the region of elevated copy number begins proximally on clone RMC20B4097 ("4097") and is highest in copy number at the most distal part of the contig, at WI-9227 (RMC20B4087, see Table 1). Copy number is not elevated at D20S120, which places the distal boundary of the new amplicon proximal to D20S120. This hybridization data confirms that a new amplicon has been identified between (proximal to distal) RMC20B4097 and D20S120 (RMC20P070).

Characterization, Isolation and Synthesis of Nucleic Acids Encoding Amplicons, Probes and Arrays This invention has for the first time provided for the localization, cloning and expression of novel nucleic acid sequences—a new amplicon—derived from human chromosome 20q13.2. The invention provides probes comprising these sequences. A further embodiment provides a means to screen for the presence of altered copy numbers of these amplicon sequences in a biological sample, particularly in human cancers. While amplicon copy numbers are commonly altered in breast cancer, they can also be diagnostic and prognostic of other cancers which include, but are not limited to, prostate, cervix, ovary, bladder, head and neck, and colon cancer.

The invention can be practiced in conjunction with any method or protocol known in the art, which are well described in the scientific and patent literature. Therefore, only a few general techniques will be described prior to discussing specific methodologies and examples relative to the novel reagents and methods of the invention.

General Techniques

Methods of isolating total DNA or RNA encoding the nucleic acids of the invention are well known to those of skill in the art. Techniques for isolation, purification and manipulation of nucleic acids, genes, probes, and amplicon sequences, such as generating libraries, subcloning into expression vectors, labeling probes, DNA hybridization, and the like are described, e.g., Sambrook; Tijssen; "CURRENT PROTOCOLS IN MOLECULAR BIOLOGY," Ausubel, ed. John Wiley & Sons, Inc., New York (1997) ("Ausubel").

The nucleic acids of this invention, whether RNA, mRNA, DNA, cDNA, genomic DNA, or a hybrid of the genetic recombinations, may be isolated from a variety of sources or may be synthesized in vitro. Nucleic acids of the invention can be expressed in, e.g., transgenic animals, transformed cells, in a transformed cell lysate, or in a partially purified or a substantially pure form. Sequencing methods typically use dideoxy sequencing (Sequenase, U.S. Biochemical), however, other kits and methods are available and well known to those of skill in the art.

Nucleic acids and proteins are detected and quantified in accordance with the teachings and methods of the invention described herein by any of a number of general means well known to those of skill in the art. These include, for example, analytical biochemical methods such as spectrophotometry, radiography, electrophoresis, capillary electrophoresis, high performance liquid chromatography (HPLC), thin layer chromatography (TLC), and hyperdiffusion chromatography, various inununological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, and the like, Southern analysis, Northern analysis, Dot-blot analysis, gel electrophoresis, RT-PCR, quantitative PCR, other nucleic acid or target or signal amplification methods, radiolabeling, scintillation counting, and affinity chromatography, to name only a few.

Synthetic Nucleic Acids

Nucleotides for use as, e.g., probes, arrays, templates for amplification, and the like, can be chemically synthesized, as described below. Synthetic nucleic acids, including oligonucleotide probes and primers, amplicon coding sequences, can be prepared by a variety of solution or solid phase methods. Detailed descriptions of the procedures for solid phase synthesis of nucleic acids by phosphite-triester, phosphotriester, and H-phosphonate chemistries are widely available. For example, the solid phase phosphoramidite triester method of Beaucage and Carruthers using an automated synthesizer is described in, e.g., Itakura, U.S. Pat. No. 4,401,796; Carruthers, U.S. Pat. Nos. 4,458,066 and 4,500,707. See also Needham-VanDevanter (1984) *Nucleic Acids Res.* 12:6159–6168; Beigelman (1995) *Nucleic Acids Res* 23: 3989–3994; OLIGONUCLEOTIDE SYNTHESIS: A PRACTICAL APPROACH, Gait (ed.), IRL Press, Washington D.C. (1984), see Jones, chapt 2, Atkinson, chapt 3, and Sproat, chapt 4; Froehler (1986) *Tetrahedron Lett.* 27:469–472; Froehler, *Nucleic Acids Res.* 14:5399–5407 (1986). Methods to purify oligonucleotides include native acrylamide gel electrophoresis, anion-exchange HPLC, as described in Pearson (1983) *J. Chrom.* 255:137–149. The sequence of the synthetic oligonucleotide can be verified using any chemical degradation method, e.g., see Maxam (1980) *Methods in Enzymology* 65:499–560, Xiao (1996) *Antisense Nucleic Acid Drug Dev* 6:247–258, or for solid-phase chemical degradation procedures, Rosenthal (1987) *Nucleic Acids Symp. Ser.* 18:249–252.

Amplification of Nucleic Acids

In various embodiments, the amplicon sequences of the invention comprise nucleic acid which hybridizes specifically to a nucleic acid sequence including from D20S211 through D20S120; nucleic acid segments spanning the distance between D20S120 and D20S211. Clones, GDB loci, STS markers, and other cloned nucleic acid segments that have been mapped within this amplicon region are set forth in Table 1, and include, e.g., nucleic acid sequence of WI-9227. The nucleic acids of the invention can be identified or generated using any amplification methodology known in the art.

Amplicon nucleic acid of the invention can be amplified using primer pairs that include or flank any segment of amplicon sequences, such as the clones, GDB loci, and STS markers set forth in Table 1. STS markers are in part defined by the primer pairs that amplify the marker, see Olson (1989) supra, and explanation above. In one embodiment, the presence and/or copy number of an amplicon of the invention is determined using PCR. In alternative embodiments, the polymerase chain reaction primer pair is an STS PCR primer pair selected from the group consisting of AFMa233wg1, AFM080ya1, AFM069ya1, WI-16748, WI-9939, AFMa072zb9, WI-6578, AFM224zd12, WI-9227, and AFM276xh1. Other PCR primer pairs to detect the presence or quantify copy number of all or a portion of the amplicon of the invention can be readily designed by the skilled artisan.

Amplification of the nucleic acid of the invention can be used for, e.g., the construction of hybridization probes, sequencing, clones, and the like. Amplification primer pairs can be used to screen for the presence of amplicon sequences in a sample of human nucleic acid. Primer pairs can be used to identify further amplicon species, such as polymorphisms, alleles and other variations, and the like.

Oligonucleotides can be used to identify, detect and amplify amplicon sequences using a variety of hybridization techniques and conditions. Suitable amplification methods include, but are not limited to: polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis)), ligase chain reaction (LCR) (Wu (1989) *Genomics* 4:560; Landegren (1988) *Science* 241:1077; Barringer (1990) *Gene* 89:117); transcription amplification (Kwoh (1989) *Proc. Natl. Acad. Sci. USA* 86:1173); and, self-sustained sequence replication (Guatelli (1990) *Proc. Natl. Acad. Sci. USA,* 87:1874); Q Beta replicase amplification and other RNA polymerase mediated techniques (e.g., NASBA, Cangene, Mississauga, Ontario); see Berger (1987) *Methods Enzymol.* 152:307–316, Sambrook, and Ausubel, as well as Mullis (1987) U.S. Pat. Nos. 4,683,195 and 4,683,202; Arnheim (1990) *C&EN* 36–47; Lomell *J. Clin. Chem.,* 35:1826 (1989); Van Brunt, *Biotechnology,* 8:291–294 (1990); Wu (1989) *Gene* 4:560; Sooknanan (1995) *Biotechnology* 13:563–564. Methods for cloning in vitro amplified nucleic acids are described in Wallace, U.S. Pat. No. 5,426,039. Methods of amplifying large nucleic acids are summarized in, e.g., Cheng (1994) *Nature* 369:684–685.

The invention provides for amplification and manipulation or detection of the products from each of the above methods to prepare DNA encoding amplicon-containing nucleic acid. In PCR techniques, oligonucleotide primers complementary to the two borders of the DNA region to be amplified are synthesized and used (see, e.g., Innis). PCR can be used in a variety of protocols to amplify, identify, quantify, isolate and manipulate nucleic acids. In these protocols, primers and probes for amplification and hybridization are generated that comprise all or any portion of the DNA sequences listed herein.

In amplifying genomic DNA, one preferred technique is degenerate oligonucleotide-primed-polymerase chain reaction ("DOP-PCR"), described by, e.g., Telenius (1992) *Genes Chromosomes Cancer* 4:257–263; Telenius (1992) *Genomics* 13:718–725; Xiao (1996) *Cytogenet. Cell Genet.* 75:57–62. DOP-PCR employs oligonucleotides of partially degenerate sequence. This degeneracy, together with a PCR protocol utilizing a low initial annealing temperature, ensures priming from multiple, e.g., approximately $10^6$ in human, evenly dispersed sites within a given genome.

Another preferred technique for amplifying genomic DNA is by linker-adapter PCR, as described by, e.g., Lucito (1998) *Proc. Natl. Acad. Sci. USA* 95:4487–4492; Miyashita (1994) *Cytogenet. Cell Genet.* 66:54–57; Vooijs (1993) *Am. J. Hum. Genet.* 52:586–597. In this procedure, DNA is extracted from the sorted chromosomes, digested to completion by using a frequently cutting restriction endonuclease (e.g., Sau3A1), and ligated, on each end, to an adaptor oligonucleotide. These fragments are then amplified using PCR with a sequence homologous to the adaptor oligonucleotide as a primer. Large amounts of highly reproducible "representations" of tumor and normal genomes can be made by PCR from nanogram amounts of restriction endonuclease cleaved DNA that has been ligated to oligonucleotide adaptors.

PCR-amplified sequences can also be labeled and used as detectable oligonucleotide probes (however, the nucleic acid probes of the invention can be generated using any synthetic or other technique well known in the art, as described herein). The labeled amplified DNA or other oligonucleotide or nucleic acid of the invention can be used as probes to further identify and isolate, or identify and quantify, amplicon sequences from any source of nucleic acid, including, RNA, cDNA, genomic DNA, genomic libraries, in situ nucleic acid, and the like.

Clones

Another useful means of obtaining nucleic acids of the invention is to screen and clone inserts isolated (or amplified) from, e.g., genomic or cDNA clones or the complete genomic clones. These include genomic or cDNA libraries contained in, e.g., mammalian artificial chromosomes (see, e.g., Ascenzioni (1997) *Cancer Lett.* 118:135–142) (including human artificial chromosomes, see, e.g., Warburton (1997) *Nature* 386:553–555; Roush (1997) *Science* 276:38–39; Rosenfeld (1997) *Nat. Genet.* 15:333–335); yeast artificial chromosomes (YAC); bacterial artificial chromosomes (BAC); PI artificial chromosomes (Woon (1998) *Genomics* 50:306–316; Boren (1996) *Genome Res.* 6:1123–1130); PACs (a bacteriophage P1-derived vector, see, e.g., Ioannou (1994) *Nature Genet.* 6:84–89; Reid (1997) *Genomics* 43:366–375; Nothwang (1997) *Genomics* 41:370–378); cosmids, plasmids or cDNAs. BACs are vectors that can contain 120+Kb inserts. BACs are based on the *E. coli* F factor plasmid system and simple to manipulate and purify in microgram quantities. Because BAC plasmids are kept at one to two copies per cell, the problems of rearrangement observed with YACs, which can also be employed in the present methods, are eliminated. BAC vectors can include marker genes, such as, e.g., luciferase and green fluorescent protein genes (Baker (1997) *Nucleic Acids Res* 25:1950–1956). YACS can also be used and contain inserts ranging in size from 80 to 700 kb, see, e.g., Tucker (1997) *Gene* 199:25–30; Adam (1997) *Plant J.* 11:1349–1358. P1 is a bacteriophage that infects *E. coli* that can contain 75–100 Kb DNA inserts (Mejia (1997) *Genome Res* 7:179–186; Ioannou (1994) *Nat Genet* 6:84–89), and are screened in much the same way as lambda libraries.

Sequencing of Nucleic Acid

Sequencing of newly isolated DNA will identify and characterize amplicon-encoding nucleic acid of the invention. Sequencing of isolated amplicon-encoding nucleic acid will also identify possible functional characteristics of the sequences, such as, e.g., coding sequences for oncogene polypeptides, transcriptional regulatory elements (e.g., promoters, enhancers), and the like.

Amplicon-encoding nucleic acid sequences can be sequenced as inserts in vectors, as inserts released and isolated from the vectors or in any of a variety of other forms (i.e., as amplification products). Inserts can be released from the vectors by restriction enzymes or amplified by PCR or transcribed by a polymerase. For sequencing of the inserts, primers based on the N- or C-terminus, or based on insertion points in the original phage or other vector, can be used. Additional primers can be synthesized to provide overlapping sequences. A variety of nucleic acid sequencing techniques are well known and described in the scientific and patent literature, e.g., see Rosenthal (1987) supra; Arlinghaus (1997) *Anal. Chem.* 69:3747–3753, for use of biosensor chips for sequencing; Pastinen (1996) *Clin. Chem.* 42:1391–1397; Nyren (1993) *Anal. Biochem.* 208:171–175. Infrared matrix-assisted laser desorption/ionization (MALDI) mass spectrometry can also be used to sequence large nucleic acid segments, such as genomic clones; see, e.g., Berkenkamp (1998) *Science* 281:260–262.

Labeling Nucleic Acid

Methods of labeling nucleic acids are well known to those of skill in the art (see definition of "labeled with a detectable composition," described above). Preferred labels are those that are suitable for use in arrays and in situ hybridization. In one embodiment, the nucleic acid probes or samples of the invention are detectably labeled prior to the hybridization reaction. Alternatively, a detectable label which binds to the hybridization product may be used. Such detectable labels include any material having a detectable physical or chemical property, such as those in the field of immunoassays. The particular label used is not critical to the present invention, so long as it does not interfere with array-based or in situ hybridization of the probe. However, probes directly labeled with fluorescent labels (e.g. fluorescein, Texas red etc.) are preferred for chromosomal DNA hybridization. In a preferred embodiment, the label is detectible in as low copy number as possible to maximize the sensitivity of the assay and yet be detectible above any background signal. The label preferably has a highly localized signal to provide a high degree of spatial resolution, especially when physically mapping the stain against a chromosome (as, e.g., a metaphase chromosome). Thus, particularly preferred fluorescent labels include fluorescein-12-dUTP and Texas Red-5-dUTP (see Example 1, below).

In various embodiments, the labels may be coupled to the probes in a variety of means known to those of skill in the art. In a various embodiments, the nucleic acid probes are labeled using nick translation, PCR, or random primer extension (see, e.g., Sambrook).

Amplicon Probes

The invention provides nucleic acid probes for screening for the presence of an amplicon in a sample of human genomic nucleic acid. In various embodiments, the probe comprises a nucleic acid which hybridizes specifically to a nucleic acid sequence: including from D20S211 through D20S120; and, spanning the distance between D20S120 and D20S211. Any probe which hybridizes to these amplicon regions are suitable for use in detecting the corresponding regions in samples, see Table 1. Methods of preparing probes are well known to those of skill in the art (see, e.g. Sambrook or Ausubel).

In one embodiment, the probe of the invention comprises a nucleic acid which hybridizes specifically to a STS marker selected from the group consisting of AFMa233wg1 (Genbank Accession No. Z52636), AFM080ya1 (Genbank Accession No. Z27067), AFM069ya1, WI-16748 (Genbank Accession No. G24133), WI-9939 (Genbank Accession No. G11766), AFMa072zb9 (Genbank Accession No. Z51873), WI-6578 (Genbank Accession No. G06115), AFM224zd12 (Genbank Accession No. Z66824), WI-9227 (Genbank Accession No. G07189), and AFM276xh1 (Genbank Accession No. Z17202).

Another embodiment provides a probe comprising nucleic acid which hybridizes specifically to a GDB locus nucleic acid sequence selected from the group consisting of D20S211 (Genbank Accession No. Z27067), D20S854 (Genbank Accession No. Z52636), D20S876 (Genbank Accession No. Z53258), D20S1044, D20S913 (Genbank Accession No. Z51873), D20S720, and D20S120 (Genbank Accession No. Z17202).

A further embodiment provides a probe comprising nucleic acid which hybridizes specifically to a cloned genomic nucleic acid sequence selected from the group consisting of RMC20B4097, RMC20B4103, RMC20P4016, RMC20B4130, RMC20P4185, RMC20B4188, RMC20B4109, RMC20P4010, RMC20P4028, RMC20P4003, RMC20B4099, RMC20P4018, RMC20P4069, RMC20B4121, RMC20B4087, and RMC20P4070.

The invention also provides a probe for screening for the presence of an amplicon in a sample comprising a polymerase chain reaction primer pair capable of amplifying some or all of the nucleic acid sequence including from D20S211 through D20S120. In one embodiment, the polymerase chain reaction primer pair is an STS PCR primer pair selected from the group consisting of AFMa233wg1, AFM080ya1, AFM069ya1, WI-16748, WI-9939, AFMa072zb9, WI-6578, AFM224zd12, WI-9227, and AFM276xh1.

The probes can be prepared by combining and labeling one or more of the amplicon nucleic acid sequences, or clones containing such sequences, as disclosed herein. If in situ hybridization methodology is used to detect amplicon sequences, the constructs are fragmented to provide smaller nucleic acid fragments that easily penetrate the cell and hybridize to the target nucleic acid. Fragmentation can be by any of a number of methods well known to those of skill in the art. Preferred methods include treatment with a restriction enzyme to selectively cleave the molecules, or alternatively to briefly heat the nucleic acids in the presence of $Mg^{2+}$. In many cases, a labeling process such as nick translation can provide probes of appropriate length. Probes are preferably fragmented to an average fragment length ranging from about 50 base pair (bp) to about 2000 bp, more preferably from about 100 bp to about 1000 bp and most preferably from about 150 bp to about 500 bp.

Nucleic Acid Hybridization Techniques

The hybridization techniques disclosed herein can be used in the methods of the invention to screen for the presence of an amplicon in a sample of human nucleic acid. Hybridization using the amplicon of the invention can also detect copy number changes in 20q13.2, which is indicative of the presence of and/or prognosis of a large number of cancers. These include, but are not limited to breast, prostate, cervix, ovary, bladder, head and neck, and colon. The methods comprise contacting the human nucleic acid with a probe (containing amplicon sequence) under stringent hybridization conditions (see definitions, above), detecting the formation of hybridization complexes, and quantifying the amplicon copy number in the sample. Hybridization techniques can also be utilized to identify, isolate and characterize amplicon genes and gene products (i.e., mRNA, encoding, e.g., oncogenes), including amplicon species, isoforms, alleles and polymorphisms. A variety of methods for specific DNA and RNA measurement using nucleic acid hybridization techniques are known to those of skill in the art. See. e.g., NUCLEIC ACID HYBRIDIZATION, A PRACTICAL APPROACH, Ed. Hames, B. D. and Higgins, S. J., IRL Press, 1985; Sambrook.

One method for evaluating the presence or absence of amplicon-encoding nucleic acid in a sample involves a Southern transfer. In a Southern Blot, a genomic or cDNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the tumor genome containing amplicon sequences) provides an estimate of the relative copy number of the target nucleic acid.

Similarly, a Northern transfer can be used for the detection of RNA containing amplicon sequences. For example, RNA is isolated from a given cell sample using an acid guanidinium-phenol-chloroform extraction method. The RNA is then electrophoresed to separate different species and transferred from the gel to a nitrocellulose membrane. As with the Southern transfers, labeled probes or PCR can be used to identify the presence or absence of amplicon nucleic acid.

Sandwich assays are commercially useful hybridization assays for detecting or isolating protein or nucleic acid. Such assays utilize a "capture" nucleic acid or protein that is often covalently immobilized to a solid support and a labeled "signal" nucleic acid, typically in solution. A clinical or other sample provides the target nucleic acid or protein. The "capture" nucleic acid or protein and "signal" nucleic acid or protein hybridize with or bind to the target nucleic acid or protein to form a "sandwich" hybridization complex. To be effective, the signal nucleic acid or protein cannot hybridize or bind substantially with the capture nucleic acid or protein.

Typically, oligonucleotide probes are labeled signal nucleic acids that are used to detect hybridization. Complementary probe nucleic acids or signal nucleic acids may be labeled by any one of several methods typically used to detect the presence of hybridized polynucleotides. Methods of detection can use any label, as described above. In a preferred embodiment of the invention, the sample nucleic acid is labeled with Texas red or fluorescein. Other labels can include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal, i.e., antibody-antigen or complementary nucleic acid binding. The label may also allow indirect detection of the hybridization complex. For example, where the label is a hapten or antigen, the sample can be detected by using antibodies. In these systems, a signal is generated by attaching fluorescent or radioactive label or enzymatic molecule to the antibodies. The sensitivity of the hybridization assays can be enhanced through use of a target nucleic acid or signal amplification system which multiplies the target nucleic acid or signal being detected. Alternatively, sequences can be generally amplified using nonspecific PCR primers and the amplified target region later probed for a specific sequence indicative of a mutation.

In situ Hybridization

An alternative means for determining the copy number of an amplicon sequence or the level of expression of a protein-encoding amplicon is in situ hybridization. In situ hybridization assays are well known (e.g., Angerer (1987) *Methods Enzymol* 152:649). Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and their conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The probes are typically labeled, i.e., with radioisotopes or fluorescent reporters. In some applications it is necessary to block the hybridization capacity of repetitive sequences. In this case, human genomic DNA or Cot-1 DNA is used to block non-specific hybridization. The preferred size range is from about 200 bp to about 1000 bases, more preferably between about 400 to about 800 bp for double stranded, nick translated nucleic acids. Hybridization protocols suitable for use with the methods of the invention are described, e.g., in Albertson (1984) *EMBO J.* 3:1227–1234; Pinkel (1988) *Proc. Natl. Acad. Sci. USA* 85:9138–9142; EPO Pub. No. 430,402; in *Methods in Molecular Biology, Vol. 33: In Situ Hybridization Protocols,* Choo, ed., Humana Press, Totowa, N.J. (1994). In a particularly preferred embodiment, the hybridization protocol of Kallioniemi (1992) *Proc. Natl Acad Sci USA* 89:5321–5325 (1992) is used.

Nucleic Acid Arrays

Nucleic acid hybridization assays for the detection of amplicon-containing sequences, for quantifying copy number, for sequencing, and the like, can also be performed in an array-based format. Arrays are a multiplicity of different "probe" or "target" nucleic acids (or other compounds) hybridized with a sample nucleic acid. In an array format a large number of different hybridization reactions can be run essentially "in parallel." This provides rapid, essentially simultaneous, evaluation of a large number of loci. Methods of performing hybridization reactions in array based formats are also described in, e.g., Pastinen (1997) *Genome Res.* 7:606–614; (1997) Jackson (1996) *Nature Biotechnology* 14:1685; Chee (1995) *Science* 274:610; WO 96/17958.

The array nucleic acid probes fixed to a solid surface. These probes comprise portions of all the amplicons of the invention, as well as probes form other portions of the genome. Amplicon nucleic acid can be obtained from, e.g., MACs, YACs, BACs, PACs, P1s, cosmids, plasmids, described above), inter-Alu PCR products of genomic clones, restriction digests of genomic clone, cDNA clones, amplification (e.g., PCR) products, and the like. In various embodiments, the array nucleic acids are derived from previously mapped libraries of clones spanning or including the amplicon sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff (1987) *Anal. Biochem.,* 164:336–344; Kremsky (1987) *Nucl. Acids Res.* 15:2891–2910). Modified nucleotides can be placed on the target using PCR primers containing the modified nucleotide, or by enzymatic end labeling with modified nucleotides. Use of membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

To optimize a given assay format, one of skill can determine sensitivity of label (e.g., fluorescence) detection for different combinations of membrane type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Target elements of various sizes, ranging from 1 mm diameter down to 1 um can be used with these materials. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup (1994) *Cytometry* 16:206–213).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258:1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, probe nucleic acid is spotted onto a surface (e.g., a glass or quartz surface). The nucleic acid is dissolved in a mixture of dimethylsulfoxide (DMSO) and nitrocellulose and spotted onto aminosilane coated glass slides. Small capillaries tubes can be used to "spot" the probe mixture.

Comparative Genomic Hybridization (CGH) Using Nucleic Acid Arrays

Comparative genomic hybridization (CGH) can detect and map DNA sequence copy number variation throughout the entire genome in a single experiment. In one variation of CGH, the genome is provided as a cytogenetic map through the use of metaphase chromosomes. In a preferred embodiment, in place of metaphase chromosomes, the hybridization probes are arrays of genomic sequences containing the amplicon sequences of the invention (as well as other sequences of the genome, as described in detail in Example 1). Relative copy number can also be measured by hybridization of fluorescently labeled test and reference nucleic acids in both metaphase chromosome-based and array-based CGH.

In metaphase chromosome-based CGH total genomic DNA is isolated from a "test" and a "reference" cell population, labeled with different fluorochromes, and hybridized to normal metaphase chromosomes. Cot-1 DNA is used to suppress hybridization of repetitive sequences. The resulting ratio of the fluorescence intensities of the two fluorochromes at a location on a chromosome is approximately proportional to the ratio of the copy numbers of the corresponding DNA sequences in the test and reference genomes. Thus, CGH provides genome-wide copy number analysis referenced to the cytogenetic map provided by the metaphase chromosomes. However, the use of metaphase chromosome CGH limits the resolution to 10–20 megabases (Mb), prohibits resolution of closely spaced aberrations, and only allows linkage of CGH results to genomic information and resources with cytogenetic accuracy.

Thus, in a preferred embodiment, a similar hybridization methodology is used with an array of mapped clones containing amplicon sequence-containing nucleic acid (or genomic nucleic acid flanking the region of interest, if positionally mapping an amplicon sequence). This permits measurement of amplicon copy number with resolution determined by the size of the clones and/or the map spacing between them. In array-based CGH, the resolution is determined by the genomic spacing of the target clones. Use of overlapping clones from regions of contiguous clone coverage as probes allows mapping with a genomic resolution less than the clone length (as low as 50 Kb). Thus, it is now possible both to map the extent of an amplicon relative to the physical map of the human genome. This methodology also quantitatively measures the amplification level of the amplicon and subregions within the amplicon. Furthermore, it is feasible to carry out these analyses on a large number of samples (e.g., tumor or other tissue samples), since the analysis time is much shorter than with metaphase chromosome-based CGH. This increases both the rate and resolution with which regions of recurrent aberration (e.g., amplification, translocation) can be identified and copy numbers ascertained.

Array CGH has shown that some tumors have uniformly high amplicon copy numbers across a single region, while others showed continuous changes in copy number extending over several hundred kilobases. These variations in copy number within an amplified region may be due to amplification processes that involve progressive "trimming" of the amplified segment as copy number is increased, as is sometimes seen with in vitro systems under drug selection. Thus, the amplification-driving nucleic acid sequence, or "critical sequence," will be found at the location of highest copy number within an amplicon. After many amplification events, the "critical gene" (the minimal amplicon sequence) will remain after non-driving segments have been "trimmed." The invention identifies a novel critical minimal amplicon sequence in the 20q13.2 region of chromosome 20.

Amplicons of the invention present in high copy numbers can also be used to identify transcribed and/or translated sequences, such as, e.g., oncogene-encoding sequences. One of the central steps in evaluating candidate oncogenes from an amplified region is assessing their expression. Tumors can be screened using the probes of the invention to identify possible oncogene transcriptional products, i.e., mRNA.

Hybridization of tumor samples imbedded in paraffin with the probes of the invention permits rapid identification of amplicon transcriptional products. Furthermore, hybridization in situ to mRNA permits evaluation of gene expression in many different tumors in a single hybridization. This high throughput method will very substantially accelerate the process of obtaining expression data from candidate oncogenes.

The 20q13.2 Region of Human Chromosome 20

The invention has identified novel amplicon sequences on human chromosome 20q13.2. In alternative embodiments, the isolated amplicon sequences of the invention, used, e.g., as probes, comprise nucleic acid segments which hybridize specifically to a nucleic acid sequence including from D20S211 through D20S120; and, spanning the distance between D20S120 and D20S211. The probes of the invention can comprise nucleic acid which hybridizes specifically to any nucleic acid sequence spanning the distance between D20S120 and D20S211; to any clone, GDB locus or STS marker in the 20q13.2 region, such as the exemplary clones, GDB loci, STSs, and other markers (e.g., WI-9227) listed in Table 1.

When modified in copy number, the amplicons of the invention are associated with cancer, especially human breast cancer. The more aggressive a tumor, the more likely it will have high a amplicon copy number. Thus, the invention provides novel probes comprising these amplicon sequences for diagnosing, prognosing and treating cancer. A few exemplary loci and markers useful in characterizing the novel amplicon of the invention are characterized below. See Table I for further clones, GDB loci, STS and other markers which can be used to characterize the novel amplicon segments of the invention.

D20S120

D20S120 is a GDB marker mapped to the 20q13 region of human chromosome 20, as described by, e.g., Weissenbach (1992) "A second-generation linkage map of the human genome," *Nature* 359:794–801; Gyapay (1994) "The 1993–94 Genethon human genetic linkage map," *Nature Genet.* 7(2 Spec No):246–339. It has also been referred to as clone AFM276xh1 or RH361. D20S120 sequence is deposited (Genbank Accession No:Z17202). Its STS marker designation is AFM276xh1, see Table 1.

D20S211

D20S211 is a GDB marker mapped to the 20q13 region of human chromosome 20, as described by, e.g., Gyapay (1994) supra. Its STS marker is AFM080ya1, see Table 1. D20S211 sequence is deposited (Genbank Accession No:Z27067).

WI-9227

WI-9227 is a 1319 base pair amplimer marker mapped to the 20q13 region of human chromosome 20. WI-9227 sequence is deposited (Genbank Accession No.:G07189).

D20S913

D20S913 is a GDB marker mapped to the 20q13 region of human chromosome 20, as described by, e.g., Dib (1996) "A comprehensive genetic map of the human genome based on 5,264 microsatellites," *Nature* 380:152–154. Its STS designation is AFMa072zb9, see Table 1. D20S913 sequence is deposited (Genbank Accession No:Z51873).

Kits Containing Probes.

This invention also provides diagnostic kits for the detection of chromosomal abnormalities or alterations in amplicon copy number on chromosome 20. In a preferred embodiment, the kits include one or more probes to the amplicons of the invention. The kits can additionally include blocking nucleic acid (i.e., Cot-1 DNA) and instructional materials describing when and how to use the kit contents. The kits can also include one or more of the following: various labels or labeling agents to facilitate the detection of the probes, reagents for the hybridization including buffers, a metaphase spread, bovine serum albumin (BSA) and other blocking agents, tRNA, SDS sampling devices including fine needles, swabs, aspirators and the like, positive and negative hybridization controls and so forth.

EXAMPLES

The following examples are offered to illustrate, but not to limit the present invention.

Example 1

High Resolution Comparative Genomic Hybridization Methodology

The invention provides a method for screening for the presence of an amplicon of the invention in a sample of human nucleic acid. The method comprises contacting the nucleic acid with an amplicon sequence-containing probe under conditions in which the probe can bind selectively under stringent conditions to amplicon sequences, and detecting the formation of the hybridization complex. The following example details a preferred methodology—"high-resolution, array-based comparative genomic hybridization (CGH)"—which can detect a single copy number difference between samples.

High Resolution Array-Based Comparative Genomic Hybridization Apparatus

The invention provides novel features to a high-resolution array CGH methodology that contribute to improved capabilities. High densities of probe DNA are attached to array substrates. The substrates are typically glass or quartz microscope slides. Quartz slides are preferred because they have much lower intrinsic fluorescence than glass, and thus produce less background light that might interfere with fluorescence measurements. Glass slides can also be used, they are less expensive and provide adequate performance.

Fluorescence signals from the arrays are acquired using a custom built large field of view imaging system (wide field imaging system) equipped with a CCD camera. A fused silica or quartz substrate containing an array is illuminated by excitation light from the back side through a prism. The excitation light, supplied by an arc lamp through collimating lens (all below the slide), passes through the array target elements (with sample nucleic acid hybridized to fixed probe). It undergoes total internal reflection off of the upper surface of the coverslip and back through the array. A mirror reflects it back into the prism. Thus only excitation light scattered by imperfections in the optical surfaces passes through the cover slip and enters the detection lenses (above the slide). Fluorescence is collected (detected) by a pair of camera lenses. The first one collects fluorescent emission from the targets, and puts out parallel light. This passes through the emission filter which selects the wavelength band of the fluorochrome being imaged. The second lens focuses the collected light onto the CCD chip. Use of a pair of lenses with the same focal lengths results in a 1× magnification (Wittrup (1994) supra).

Array printing technology is focused on increasing printing speed to facilitate array manufacture, and decreasing the physical size of the arrays to minimize the amount of specimen nucleic acid required for hybridization. A basic approach is to use a print head with multiple printing tips, so that many different targets can be printed in parallel. This reduces the time required to print the array. As a brief overview of the array robot, the print head is carried on a high speed overhead gantry between the microtiter plate feeder and the printing position. Array substrates are positioned under the print head with an X-Y stage. Printing pins are washed at a station located between the plate feeder and the stage. A nine pin print head is used in the form of a 3×3 array of spring mounted capillary tubes on 3 mm centers for printing out of a 864 well microtiter plate. Each capillary is connected to a manifold by flexible tubing through which vacuum or pressure can be supplied. Vacuum is used to draw cleaning solutions through the tips and to load them with printing solutions, while a slight pressure is applied during printing.

Preparing Nucleic Acid Samples for Array Analysis

Nucleic acid from any biological can be used to prepare labeled sample for analysis. For example, for biopsies of breast tissue, snap-frozen blocks of suspected primary breast tumor tissue can be cryosectioned, typically at about 4 microns, and stained, e.g., with hematoxylin and eosin to determine the ratio of malignant to non-malignant cells within the section. Areas containing normal ducts and lobules that are removable by block trimming are marked on the slide. The block is aligned with the section on the slide and trimmed with a cold razor blade. The next 10 to 20 sections of the trimmed block are collected in a microfuge tube for DNA extraction. The DNA can be isolated, e.g., using QUIamp tissue kits (#29304), following the instructions of the manufacturer. Lysis times can be extended, if necessary, depending on the condition of the tissue. The samples are also incubated with RNAase A. DNA is eluted from the column in water after 5 min incubation at 70° C. A second elution step can be used to increase yield, if needed.

This sample, or test, nucleic acid is labeled with fluorescein. Reference DNA is labeled with another reagent, typically with Texas red. The labeling is done by nick translation according to standard procedures and manufacturer's instructions.

Array Probes

Cloned genomic DNA for use as probes can be produced by any protocol known in the art, as described above, including, e.g., recombinant or PCR amplification technologies. PCR amplification is facilitated by STS primer pair information in public databases, see, e.g., Olson (1989) supra. Traditional recombinant technology can also be used. For example, MACs, YACs, BACs, PACs, P1s, cosmids, plasmids or cDNAs containing probe sequences can be generated. In one exemplary protocol, plasmids are isolated from 500 ml cultures of bacteria using QIAGEN maxi kits (#12162) following the instructions of the manufacturer except that the volume of lysis buffer is increased about 1.5 to 2 fold. The DNA is resuspended in 400 ul TE buffer (10 mM Tris, 1 mM EDTA, pH 8), extracted with phenol, chloroform, isoamyl alcohol (25:24:1 ratio). It is then precipitated with ethanol. After resuspension in TE buffer, the DNA concentration is determined using a fluorometer (e.g., a Hoefer TKO 100). This procedure typically yields 40 to 80 ug of P1 or BAC DNA that is of sufficient purity to produce nucleic acid that bind effectively to the slides and have acceptably low autofluorescence.

Arrays for the studies presented below were made by dissolving the probe DNA in a mixture of water, dimethysulfoxide (DMSO) and nitrocellulose and depositing nanoliter amounts of the resulting solutions onto amino-silane coated array substrates with glass or quartz capillaries. Probe solutions are made by precipitating 10 ug of DNA in ethanol and dissolving the pellet in 1 ul of water, followed by addition of 4 ul of DMSO containing approximately 0.4 ug/ul of nitrocellulose. The nitrocellulose solution is prepared by dissolving a nitrocellulose membrane (Gibco BRL #41051-012) in DMSO. The nitrocellulose substantially improved the ability to retain hybridizable DNA fragments of length greater than several kilobases in the targets, however smaller fragments were not bound effectively.

Glass, quartz or fused silica slides are cleaned by incubation in 50% concentrated sulfuric acid, 50% hydrogen peroxide overnight. They are then washed 10× in distilled water, air dried and heated to 90° C. for 15 min. The surfaces of the cleaned slides are coated by immersion in 95% acetone with 0.1% aminopropyltrimethoxy silane for 2 min at room temperature, after which they are washed 5× in acetone and air dried.

The resulting probe target elements were primarily DNA, containing less than 15% nitrocellulose by mass. Autofluorescence from the target elements was negligible. No additional denaturing of probe DNA was required prior to hybridization.

Hybridization

For hybridization, a low barrier was formed around the array with rubber cement. The resulting well is about 0.6 to 1 cm$^2$ in area. The hybridization mix typically contains approximately 400 nanogram (ng) each of test and reference DNA. Test DNA is labeled with fluorescein and reference DNA with Texas red (as described above). In a typical hybridization reaction, 200 to 400 ng of labeled test (human nucleic acid sample) and reference labeled DNA are mixed. About thirty-five (35) to about fifty (50) ug of Cot-1 (Gibco BRL) DNA is also included in the hybridization mix to block the repetitive sequences. This mixture is then precipitated with ethanol. It is critical to determine the amount of Cot-1 by fluorometric means (e.g., a Hoeffer TKO 100 fluorimeter) since absorption measurements of concentration used by the commercial suppliers frequently overestimate the effective amount of blocking DNA present by a factor of 3 to 6. Use of too little blocking DNA substantially reduces the ability to detect small ratio changes.

The precipitated DNA is dissolved in 10 ul of hybridization mix to achieve a final composition of 50% formamide, 10% dextran sulfate, 2×SSC, 2% SDS and 100 ug tRNA. The well is filled with 10 ul of this hybridization mix. No coverslip is used. The hybridization solution is heated to 70° C. for 5 min to denature the DNA, and then incubated at 37° C. for approximately 1 hour to allow blocking of the repetitive sequences. The hybridization proceeded at 37° C. for 16 to 72 hours on a slowly rocking table to actively transport the hybridization mix over the targets. The slide is placed in a small sealed slide box containing 200 ul of hybridization solution (50% formamide/2×SSC) without probe to prevent evaporation during the hybridization.

After hybridization, the slide is washed once in 50% formamide, 2×SSC, pH 7, at 45° C. for 15 min, and once in 0.1 M sodium phosphate buffer with 0.1% NP40, pH 8 at room temperature. Excess liquid is drained from the slides and the array mounted in an antifade solution containing 1 ug/ml of DAPI to counter stain the DNA targets. A glass coverslip is sealed in place. The slide is placed in the array apparatus and fluorescence read, as described above.

Analysis Data

Background fluorescence, as a function of location on the slide, is calculated for the probe fluorochrome images, typically fluorescein (sample DNA) and Texas red (reference DNA), and the background-corrected total fluorescein and Texas red intensities are calculated for each segmented target (fluorescence signals were analyzed with an image analysis program). The intensities of the two fluorochromes are also calculated for each target. This analysis takes approximately 1 minute. The data are then transmitted to a data base for storage and analysis by an image analysis program.

The Pearson's "r" correlation between the green and red intensities of each pixel was also calculated. Ideally one expects that the green and red intensities of each pixel in a target will be proportional to each other, so that a plot of these measurements will fall on a straight line, and the correlation would be 1.0. In practice "r" values range from near 1.0, to very low, indicating scatter in the data. Therefore we discard measurements on all spots that have a correlation below an arbitrarily determined threshold of 0.8. Thus, final ratios represent the average of the ratios of the targets that gave useful signals.

While any image analysis program can be used to make the above-indicated calculations, in these experiments a variation of the Chromosome CGH Analysis Program (Vysis, Inc., Downers Grove, Ill.) was used. Quadruplicate spots of each target clone are typically used in the arrays, as was done in these experiments. The locations of the target spots were determined by segmenting the DAPI counterstain image.

This array CGH procedure was evaluated in: (a) a model system that did not contain repetitive sequences, (b) normal human cells, and (c) a cell line containing known copy number changes. Performance in the absence of repetitive sequences was assessed using test and reference genomes consisting of 200 ng of total human genomic DNA spiked with varying amounts of lambda DNA. Since lambda DNA has a length $1.7 \times 10^{-5}$ of the human genome (50 kb vs. $3 \times 10^6$ kb), approximately 3 pg of lambda DNA is equivalent to a single copy human sequence. Test genomes contained 200 ng of human genomic DNA and 1, 2, 20, 200 and 2000 pg of lambda DNA. The ratios were normalized relative to hybridization. The reference genomes contained 200 ng of human genomic DNA and 20 pg of lambda DNA. Twenty pg of lambda DNA was used in the reference, since the reassociation of the double stranded lambda sequences at the higher test genome concentrations (200 and 2000 pg of lambda DNA) in hybridizations suppressed the reference signal and produced a corresponding sub-linear increase of the test signal. However, the ratio of the test and reference fluorescence signals increased proportionally to the ratio of the amounts of lambda DNA in the two genomes.

Simple theoretical considerations lead to the expectation that the fluorescence ratios should be accurately proportional to copy number ratios if the fluorochromes do not differentially affect the hybridization. Such performance was achieved over the entire measured range, from below single copy equivalent level to a factor of about $10^3$ higher. Therefore, copy number increases or decreases involving cosmid-sized segments of the human genome or larger should be detectable at the single copy level. Significantly, higher level changes can also be accurately quantified (if repetitive sequences do not interfere).

Single Copy Number Difference Detected

Measurements on human specimens were performed with an array that contains targets made from cosmid, P1 and BAC clones distributed along the length of chromosome 20 at approximately 3 Mb intervals, and clones from a contig spanning a 1.5 Mb region of chromosome 20q13.2. The array also contains genomic clones for the known cancer genes cMYC, cERBB2, p53 and p 16 and a clone from a region of the X chromosome. Comparison of normal male to normal female DNA was used to assess the variability in the ratio among targets that are present at the same relative copy number in the two genomes, and the ability to detect low level copy number changes. The ratios of the chromosome 20 targets, normalized to have an average value of 1.0, had ratios of 1.0+/−0.14 (standard deviation). An X chromosome target was also included and the ratio, normalized relative to chromosome 20, was 0.63+/−0.04. Therefore it was significantly lower. Thus, a single copy decrease in a diploid genome was detectable. The deviation of X chromosome ratio from the expected value of 0.5 (for a haploid copy number) was most likely due to incomplete suppression of signal from repetitive sequences.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for screening for the presence or absence of an amplicon in a sample of human nucleic acid, the method comprising:

providing a sample of nucleic acid derived from a human cell;

providing a probe, wherein the probe hybridizes specifically to a chromosomal region from D20S211 through D20S120 under wash conditions that include 0.2×SSC at 65° C.;

contacting the human nucleic acid with the probe, wherein the probe is contacted with the human nucleic acid under conditions in which the probe binds selectively under stringent conditions to the human nucleic acid to form a hybridization complex; and detecting the formation of the hybridization complex to confirm the presence or absence of the amplicon.

2. The method of claim 1, wherein the human nucleic acid is a genomic DNA.

3. The method of claim 1, wherein the step of detecting the hybridization complex further comprises determining the copy number of the amplicon.

4. The method of claim 1, wherein the human nucleic acid is isolated from a breast tumor cell.

5. The method of claim 1, wherein the probe comprises a nucleic acid which hybridizes specifically to a sequence tagged site (STS) marker selected from the group consisting of AFMa233wg1, AFM080ya1, AFM069ya1, WI-16748, WI-9939, AFMa072zb9, WI-6578, AFM224zd12, WI-9227, and AFM276xh1.

6. The method of claim 1, wherein the probe comprises nucleic acid which hybridizes specifically to a Genome Database (GDB) locus nucleic acid sequence selected from the group consisting of D20S211, D20S854, D20S876, D20S1044, D20S913, D20S720, and D20S120.

7. The method of claim 1, wherein the probe comprises nucleic acid which hybridizes specifically to a cloned genomic nucleic acid sequence selected from the group consisting of RMC20B4097, RMC20B4103, RMC20P4016, RMC20B4130, RMC20P4185, RMC20B4188, RMC20B4109, RMC20P4010, RMC20P4028, RMC20P4003, RMC20B4099, RMC20P4018, RMC20P4069, RMC20B4121, RMC20B4087, and RMC20P4070.

8. The method of claim 1, wherein the probe comprises a polymerase chain reaction primer pair which amplifies some or all of the nucleic acid sequence including from D20S211 through D20S120 and the detection step comprises detecting the formation of the polymerase chain reaction amplification reaction.

9. The method of claim 1, wherein the polymerase chain reaction primer pair is a sequence tagged site (STS) PCR primer pair selected from the group consisting of AFMa233wg1, AFM080ya1, AFM069ya1, WI-16748, WI-9939, AFMa072zb9, WI-6578, AFM224zd12, WI-9227, and AFM276xh1.

10. The method of claim 1, wherein the probe is attached to a solid surface.

11. The method of claim 10, wherein the attached probe is a member of a nucleic acid array.

12. The method of claim 1, wherein the human nucleic acid is labeled with a detectable composition.

13. The method of claim 12, wherein the detectable composition is fluorescein or Texas red.

14. The method of claim 1, wherein the probe is labeled with a detectable composition.

15. The method of claim 1, wherein the method further provides a nucleic acid from a reference cell, wherein the reference cell nucleic acid is contacted with the probe before or simultaneously with the human nucleic acid.

16. The method of claim 1, wherein the method further provides Cot-1 DNA, wherein the Cot-1 DNA is hybridized to the human nucleic acid before contacting the human nucleic acid with the probe.

* * * * *